(12) United States Patent
Sukovic

(10) Patent No.: US 7,170,968 B2
(45) Date of Patent: Jan. 30, 2007

(54) CT SCANNER SYSTEM AND METHOD FOR IMPROVED POSITIONING

(75) Inventor: Predrag Sukovic, Birmingham, MI (US)

(73) Assignee: Xoran Technologies, Inc., Ann Arbor, MI (US)

( * ) Notice: Subject to any disclaimer, the term of this patent is extended or adjusted under 35 U.S.C. 154(b) by 0 days.

(21) Appl. No.: 10/971,562

(22) Filed: Oct. 22, 2004

(65) Prior Publication Data

US 2005/0089139 A1    Apr. 28, 2005

Related U.S. Application Data

(60) Provisional application No. 60/513,409, filed on Oct. 22, 2003.

(51) Int. Cl.
*G01N 23/00* (2006.01)

(52) U.S. Cl. .......................................... 378/20; 378/205

(58) Field of Classification Search ............. 378/4–20, 378/205, 207, 208, 209, 38, 98, 98.5
See application file for complete search history.

(56) References Cited

U.S. PATENT DOCUMENTS

| | | | | |
|---|---|---|---|---|
| 5,329,567 A | * | 7/1994 | Ikebe ........................... | 378/20 |
| 5,457,724 A | * | 10/1995 | Toth ............................... | 378/4 |
| 6,493,415 B1 | * | 12/2002 | Arai et al. ....................... | 378/4 |
| 6,827,489 B2 | * | 12/2004 | Nicolas et al. .............. | 378/205 |
| 2002/0048347 A1 | * | 4/2002 | Saito ............................ | 378/207 |
| 2003/0223532 A1 | | 12/2003 | Clinthorne et al. | |
| 2003/0235265 A1 | | 12/2003 | Clinthorne et al. | |

* cited by examiner

*Primary Examiner*—Edward J. Glick
*Assistant Examiner*—Hoon Song
(74) *Attorney, Agent, or Firm*—Carlson, Gaskey & Olds

(57) ABSTRACT

The CT scanning system of the present invention includes a source and detector mounted to a c-arm. The c-arm is positioned on a mounting plate and ball screw to rotate about an axis centered within the c-arm and to also translates along the axis of rotation. A computer controls the rotation of the CT scanner, the x-ray source, and collects the data from the detector to create an image. The CT scanner first takes a scout scan prior to the full acquisition of the data. The scout scan is a single two-dimension image. The CPU draws locating marks on the scout scan image to indicate the desired location. When proper alignment is verified, the processor then controls the motor to perform one complete revolution of the c-arm, during which time the computer collects multiple images from the detector.

12 Claims, 2 Drawing Sheets

CT SCANNER SYSTEM AND METHOD FOR IMPROVED POSITIONING

This application claims priority to U.S. Provisional Patent Application Ser. No. 60/513,409, filed Oct. 22, 2003.

BACKGROUND OF THE INVENTION

Computed tomography (CT) scanners are used to provide information regarding internal organs of a patient. For example, CT scanners are often used to gather information regarding sinus cavities within a patient's head.

The CT scanner includes an x-ray source and an x-ray detector on opposite sides of the patient's body near the area to be scanned. Current CT systems require the patient to be positioned relative to the x-ray source in order to obtain a clear image. The x-ray from the x-ray source is collimated to emit a fan-beam x-ray producing a plurality of "slices" through the patient's body as the x-ray source and detector revolve around the patient's body.

Because the x-ray source is a fan-beam x-ray source, imaging only a narrow slice at a time, it is difficult to determine the correct position of the patient. When the patient is in the incorrect position the patient must be moved and the CT scan repeated until a clear image can be viewed. The CT scanner is fixed in the room, so the bed, the patient and the robot must all be translated along the axis of rotation of the CT scanner to obtain the correct position.

In addition, the CT scanner exposes the doctor and the patient to radiation. In order to create a three-dimensional image the scanning device must take multiple images from different position along the patient's body. Although the doctor can avoid excessive doses of radiation by remotely controlling the system, the continuous scanning by the CT scanner exposes the patient's body to more radiation than necessary.

Therefore, a system is needed which reduces the exposure of the patient, and doctor by reducing number of images required to be taken.

SUMMARY OF THE INVENTION

The CT scanner of the present includes an x-ray source connected one end of a c-arm and a detector supported at the opposing end of the c-arm. The CT scanner also includes a computer. The center of the c-arm is supported by a motor for rotating the c-arm relative to a mounting plate. The computer controls the motor to control the rotation of the CT scanner, controls the x-ray source, and collects the data from the detector to create an image on the display.

To ensure proper positioning prior to the full scan, the CT scanner first takes a scout scan prior to the full acquisition of the data. The scout scan is a single two-dimension image. The CPU draws locating marks on the scout scan image to indicate the desired location of the patient's head. If the patient's head is not properly aligned with the locating marks, then the patient's head is repositioned based upon the scout scan. A new scout scan may then be taken to verify the position.

When proper alignment is verified, the processor then controls the motor to perform one complete revolution of the c-arm, during which time the computer collects multiple images from the detector. The images taken by the detector are stored in the memory. The computer then generates the images of the scanned body part based upon the data.

BRIEF DESCRIPTION OF THE DRAWINGS

The above, as well as other advantages of the present invention, will become readily apparent to those skilled in the art from the following detailed description of a preferred embodiment when considered in the light of the accompanying drawing in which.

DETAILED DESCRIPTION OF THE PREFERRED EMBODIMENT

Figure 1:
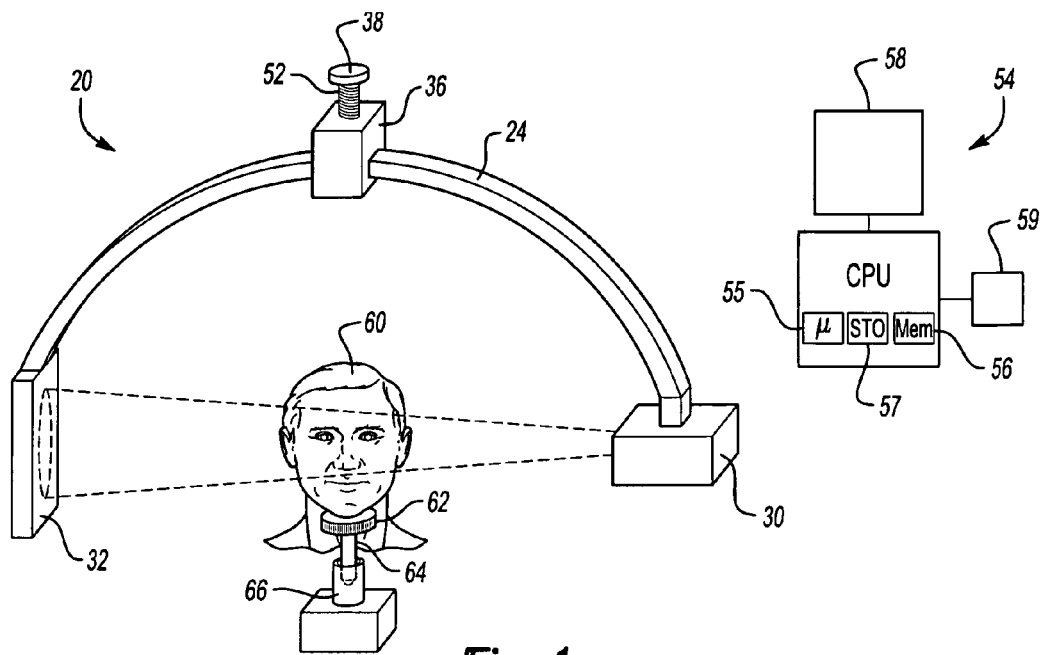
FIG. 1 is a schematic of the CT scanning system of the present invention.

A CT scanner 20 according to the present invention is illustrated in FIG. 1. The CT scanner 20 includes a c-arm 24 connected at one end to an x-ray source 30, which in this embodiment is a cone-beam x-ray source 30. The other end of the c-arm 24 supports a complementary detector 32. The detector 32 is a two-dimensional detector as shown. The center of the c-arm is supported by a motor 36 for rotating the c-arm 24 relative to a mounting plate 38. The CT scanner 20 may optionally include a ball screw 42 connecting the motor 36 to the mounting plate 38, such that during the single revolution, the CT scanner 20 also translates approximately 1 inch along the axis of rotation, thus providing additional data for the computer 54

The CT scanner 22 further includes a computer 54 including a microprocessor or CPU 55, memory 56, a hard drive 57 and/or other optical, magnetic, electronic or other mass storage, and other hardware and software for performing the functions described herein. The computer 54 also includes a display 58 and at least one input device 59 (mouse and keyboard, etc). Note that for simplicity all connections between the computer 54 and the other components in the CT scanner 20 are not shown. The processor 54 in the disclosed embodiment performs at least these three functions: First, the computer 54 controls the rotation of the CT scanner 20 by controlling the motor 36. Second, the computer 54 also controls the x-ray source 30, including powering the source 30 on and off and varying the intensity of the produced x-ray. Third, the computer 54 collects the data from the detector 32, such as in memory 56 or storage 57. The computer 54 may be on-board the c-arm 24 or may be off-board and connected via wires or wireless transmitters and receivers.

Figure 2:
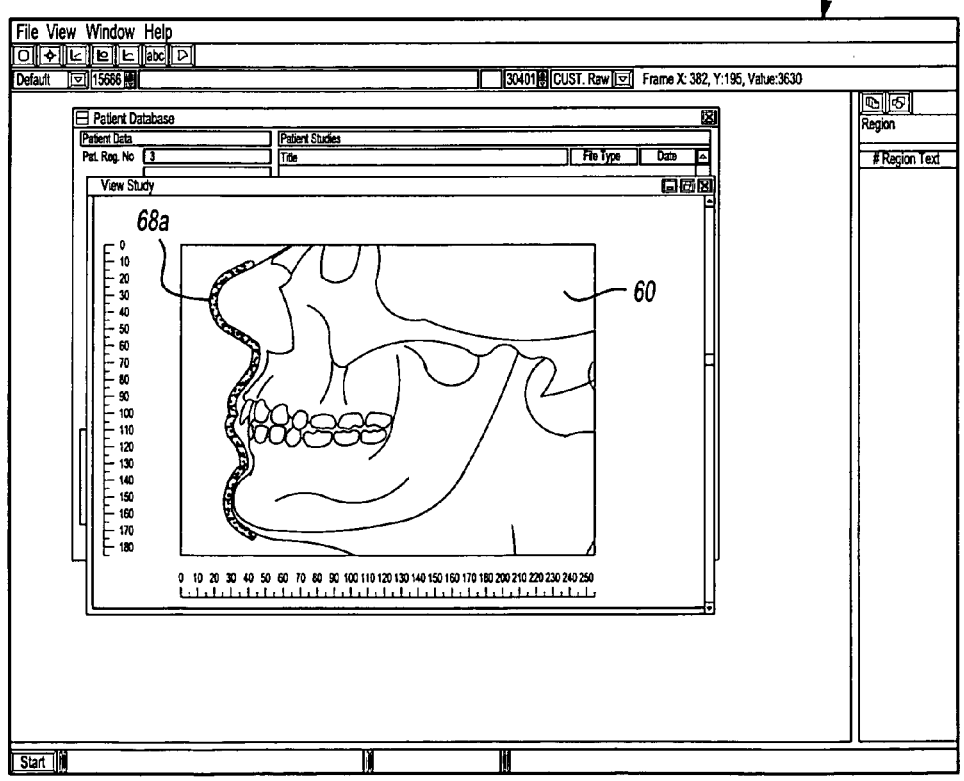
FIG. 2 illustrates a display of a scout scan taken using the CT scanning system of FIG. 1.
Figure 3:
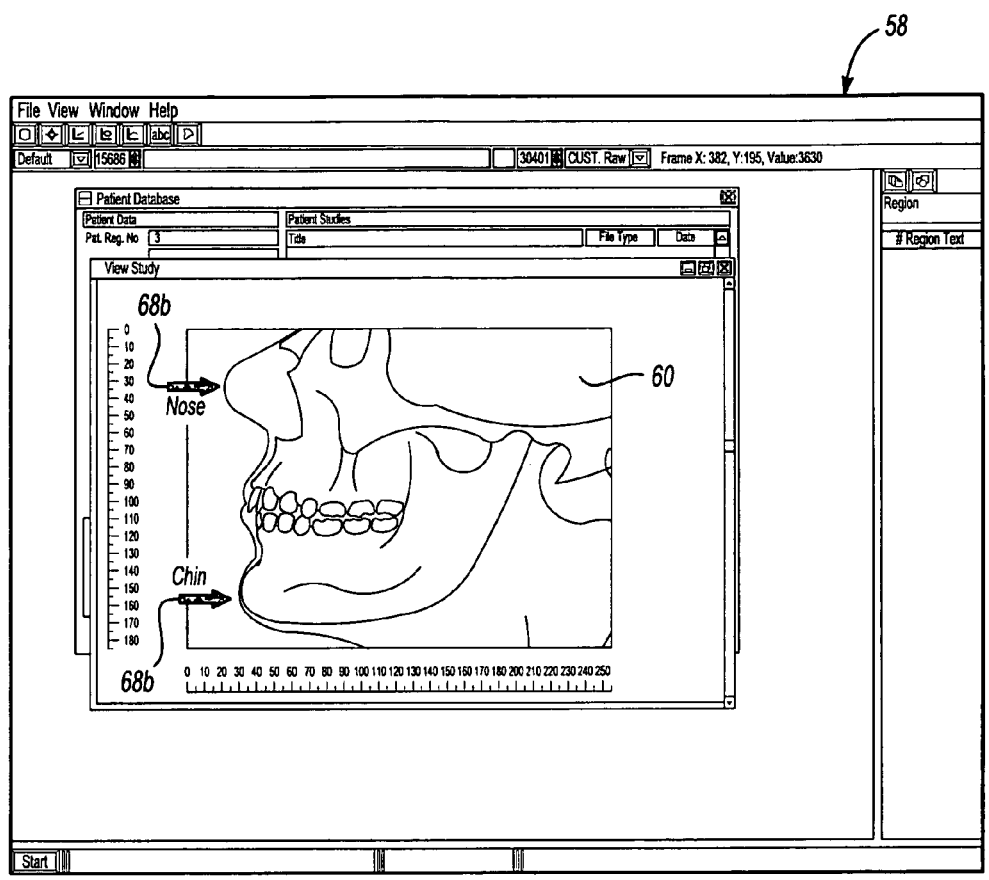
FIG. 3 illustrates a display of an alternate scout scan using the CT scanning system of FIG. 1.

One particularly useful application of the CT scanner 20 of the present invention is in scanning the sinus cavities of the patient's head 60. It is therefore important that the patient's head 60 be properly aligned between the source 30 and detector 32 (vertically as shown in FIGS. 1–3, although the CT scanner 20 could also be oriented horizontally). In operation, the part of the body to be scanned, such as the head 60, is positioned between the source 30 and detector 32. The head 60 is positioned with the chin resting on an adjustable stand 62 having on a post 64 slidably received in a base 66. This assists the patient in staying still during the scan and staying in the proper position. The computer 54 powers on the x-ray source 30 to generate a cone-beam x-ray 70 that is directed toward the detector 32.

In the present invention, the CT scanner 20 first takes a scout scan prior to the full acquisition of the data. The scout scan, shown on display 58 in FIGS. 2 and 3, is a single two-dimension image taken by the source 30 and detector 32. The scout scan could be a lower dose of x-rays than is normally used during each of the plurality of images taken during the CT scan that follows. The CPU 54 draws locating marks 68*a* (FIG. 2) or alternatively locating marks 68*b* (FIG. 3) on the scout scan image to indicate the desired location of the patient's head 60. If the patient's head 60 is not properly aligned with the locating marks 68, then the patient's head 60 is repositioned based upon the scout scan. The adjustable stand 62 may be re-positioned up or down relative to the base 66 to correct the position of the patient's head 60. A new scout scan may then be taken to verify the position before the CT scanner 20 acquires the full set of images.

When proper alignment is verified, the processor 54 then controls the motor 36 to perform one complete revolution of the c-arm 24, during which time the computer 54 collects multiple images from the detector 32. The images taken by detector 32 are stored in memory 56 and/or storage 57. The computer 60 then generates the 3-D models and/or selected 2-D images of the scanned body part based upon the data.

Although a preferred embodiment of this invention has been disclosed, a worker of ordinary skill in this art would recognize that certain modifications would come within the scope of this invention. For that reason, the following claims should be studied to determine the true scope and content of this invention.

What is claimed is:

1. A CT scanner system comprising:
   an x-ray source and a detector mounted for rotation about a patient;
   a display for generating an image based upon x-rays received by the detector, wherein the x-ray source and the detector take a two-dimensional scout scan which is displayed on the display to indicate the current position of the patient, wherein the display displays an outline relative to the scout scan to indicate the desired position of the patient relative to a current position of the patient, by displaying marks relative to the scout scan.

2. The CT scanner system of claim 1 wherein said x-ray source is a cone beam source.

3. The CT scanner system of claim 1 further including a computer for generating a three-dimensional image of the patient based upon a plurality of images taken by the detector, the computer generating an image of the scout scan to be displayed on the display.

4. The CT scanner system of claim 3 further including a rotatable arm to which the x-ray source and the detector are mounted for rotation about an axis.

5. The CT scanner system of claim 1 further including an adjustable stand for contacting the patient and for positioning the patient relative to the x-ray source and the detector.

6. The CT scanner system of claim 5 wherein the adjustable stand contacts a patient's chin.

7. A method of obtaining a CT scan including the steps of:

a) positioning a head of a patient between an x-ray source and a detector;
b) taking a scout image of the head of the patient with the x-ray source and the detector after said step a);
c) indicating a desired position of the head of the patient on a display relative to the scout image;
d) re-positioning the head of the patient relative to the x-ray source and the detector based upon the scout image by moving the head of the patient vertically at least in part parallel to an axis through the patient;
e) after said step d), rotating the source and the detector about the axis;
f) collecting a plurality of images with the detector during said step e); and
g) creating a three-dimensional image based upon the plurality of images collected in said step f).

8. The method of claim 7, wherein the scout image is a two-dimensional image.

9. The method of claim 7 wherein the x-ray source generates a lower dose of x-rays during said step b) than during the collection of one of the plurality of images during said step f).

10. The method of claim 7 further including the steps of:
    contacting the head of the patient with at least one adjustable stand during said step a); and
    adjusting the at least one adjustable stand during said step d).

11. A method of obtaining a CT scan including the steps of:

a) positioning a head of a patient between an x-ray source and a detector;
b) taking a scout image of the head of the patient with the x-ray source and the detector after said step a);
c) displaying the scout image on a display;
d) displaying at least one marker with the scout image on the display to indicate a desired position of the head of the patient relative to the scout image;
e) re-positioning the head of the patient vertically relative to the x-ray source and the detector after said step c) based upon the scout image and the at least one marker on the display;
f) after said step e), rotating the source and the detector about a vertical axis;
g) collecting a plurality of images with the detector during said step f); and
h) creating a three-dimensional image based upon the plurality of images collected in said step g).

12. The method of claim 11 wherein said step e) includes the step of adjusting a stand in contact with a chin of the patient.

* * * * *